(12) United States Patent
Mishelevich et al.

(10) Patent No.: US 9,486,639 B2
(45) Date of Patent: Nov. 8, 2016

(54) TRAJECTORY-BASED DEEP-BRAIN STEREOTACTIC TRANSCRANIAL MAGNETIC STIMULATION

(75) Inventors: David J. Mishelevich, Playa del Rey, CA (US); M. Bret Schneider, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 100 days.

(21) Appl. No.: 13/240,060

(22) Filed: Sep. 22, 2011

(65) Prior Publication Data

US 2012/0016177 A1 Jan. 19, 2012

Related U.S. Application Data

(63) Continuation of application No. 11/429,504, filed on May 5, 2006, now Pat. No. 8,052,591.

(51) Int. Cl.
*A61N 2/02* (2006.01)
*A61N 2/00* (2006.01)

(52) U.S. Cl.
CPC ............... *A61N 2/004* (2013.01); *A61N 2/006* (2013.01); *A61N 2/008* (2013.01); *A61N 2/02* (2013.01)

(58) Field of Classification Search
CPC ............ A61N 1/00; A61N 2/00; A61N 2/02; A61N 2/004; A61N 2/006; A61N 2/008; A61B 19/00
USPC ........................................ 600/9–15; 607/2, 3
See application file for complete search history.

(56) References Cited

U.S. PATENT DOCUMENTS

| | | | |
|---|---|---|---|
| 3,799,164 A | 3/1974 | Rollins | |
| 4,134,395 A | 1/1979 | Davis | |
| 4,690,130 A | 9/1987 | Mirell | |
| 4,889,526 A | 12/1989 | Rauscher et al. | |
| 5,047,005 A | 9/1991 | Cadwell | |
| 5,207,223 A | 5/1993 | Adler | |
| 5,267,938 A | 12/1993 | Konotchick | |
| 5,427,097 A | 6/1995 | Depp | |
| 5,441,495 A | 8/1995 | Liboff et al. | |

(Continued)

FOREIGN PATENT DOCUMENTS

| | | | |
|---|---|---|---|
| DE | 10242542 A1 | 4/2004 | |
| EP | 0501048 A1 | 9/1992 | |

(Continued)

OTHER PUBLICATIONS

Agnew et al.; Considerations for safety in the use of extracranial stimulation for motor evoked potentials; Neurosurgery; vol. 20; pp. 143-147; Jan. 1987.

(Continued)

*Primary Examiner* — Christine H Matthews
(74) *Attorney, Agent, or Firm* — Shay Glenn LLP

(57) ABSTRACT

The present invention provides for Stereotactic Transcranial Magnetic Stimulation (sTMS) at predetermined locations with the brain or spinal cord and incorporates an array of electromagnets arranged in a specified configuration where selected coils in the array are pulsed simultaneously. Activation of foci demonstrated by functional MRI or other imaging techniques can be used to locate the neural region affected. Imaging techniques can also be utilized to determine the location of the designated targets.

9 Claims, 6 Drawing Sheets

(56) References Cited

U.S. PATENT DOCUMENTS

| | | |
|---|---|---|
| 5,531,227 A | 7/1996 | Schneider |
| 5,707,334 A | 1/1998 | Young |
| 5,738,625 A | 4/1998 | Gluck |
| 5,766,124 A | 6/1998 | Polson |
| 5,891,034 A | 4/1999 | Bucholz |
| 6,042,531 A | 3/2000 | Holcomb |
| 6,132,361 A | 10/2000 | Epstein et al. |
| 6,132,631 A | 10/2000 | Nallan et al. |
| 6,149,577 A | 11/2000 | Bouldin et al. |
| 6,179,770 B1 | 1/2001 | Mould |
| 6,179,771 B1 | 1/2001 | Mueller |
| 6,198,958 B1 | 3/2001 | Ives et al. |
| 6,236,875 B1 | 5/2001 | Bucholz et al. |
| 6,266,556 B1 | 7/2001 | Ives et al. |
| 6,351,573 B1 | 2/2002 | Schneider |
| 6,356,781 B1 | 3/2002 | Lee et al. |
| 6,379,295 B1 | 4/2002 | Woo |
| 6,425,852 B1 | 7/2002 | Epstein et al. |
| 6,447,440 B1 | 9/2002 | Markoll |
| 6,459,924 B1 | 10/2002 | Creighton et al. |
| 6,461,289 B1 | 10/2002 | Muntermann |
| 6,488,617 B1 | 12/2002 | Katz |
| 6,507,751 B2 | 1/2003 | Blume et al. |
| 6,537,197 B1 | 3/2003 | Ruohonen et al. |
| 6,571,123 B2 | 5/2003 | Ives et al. |
| 6,572,528 B2 | 6/2003 | Rohan et al. |
| 6,663,556 B2 | 12/2003 | Barker |
| 6,818,669 B2 | 11/2004 | Moskowitz et al. |
| 6,849,040 B2 | 2/2005 | Ruohonen et al. |
| 6,858,000 B1 | 2/2005 | Schukin et al. |
| 6,926,659 B1 | 8/2005 | Sandstrom |
| 6,972,097 B2 | 12/2005 | Yoshida et al. |
| 7,023,311 B2 | 4/2006 | Baldwin et al. |
| 7,087,008 B2 | 8/2006 | Fox et al. |
| 7,088,210 B2 | 8/2006 | Day et al. |
| 7,104,947 B2 | 9/2006 | Riehl |
| 7,130,203 B2 | 10/2006 | Mbaye |
| 7,141,028 B2 | 11/2006 | McNew |
| 7,153,256 B2 | 12/2006 | Riehl et al. |
| 7,155,284 B1 | 12/2006 | Whitehurst et al. |
| 7,236,830 B2 | 6/2007 | Gliner |
| 7,239,910 B2 | 7/2007 | Tanner |
| 7,320,664 B2 | 1/2008 | Riehl et al. |
| 7,367,935 B2 | 5/2008 | Mechlenburg et al. |
| 7,367,936 B2 | 5/2008 | Myers et al. |
| 7,396,326 B2 | 7/2008 | Ghiron et al. |
| 7,437,196 B2 | 10/2008 | Wyler et al. |
| 7,483,747 B2 | 1/2009 | Gliner et al. |
| 7,520,848 B2 | 4/2009 | Schneider et al. |
| 7,670,838 B2 | 3/2010 | Deisseroth et al. |
| 7,771,341 B2 | 8/2010 | Rogers |
| 7,856,264 B2 | 12/2010 | Firlik et al. |
| 7,904,134 B2 | 3/2011 | McIntyre et al. |
| 8,052,591 B2 | 11/2011 | Mishelevich et al. |
| 2002/0022777 A1 | 2/2002 | Crieghton et al. |
| 2002/0097125 A1 | 7/2002 | Davey |
| 2003/0004392 A1 | 1/2003 | Tanner et al. |
| 2003/0028072 A1 | 2/2003 | Fischell et al. |
| 2003/0065243 A1 | 4/2003 | Tanner |
| 2003/0204135 A1 | 10/2003 | Bystritsky |
| 2004/0010177 A1 | 1/2004 | Rohan et al. |
| 2004/0077921 A1 | 4/2004 | Becker et al. |
| 2004/0078056 A1 | 4/2004 | Zangen et al. |
| 2004/0156884 A1 | 8/2004 | Brown et al. |
| 2004/0193000 A1 | 9/2004 | Riehl |
| 2004/0193002 A1 | 9/2004 | Tanner et al. |
| 2004/0204625 A1* | 10/2004 | Riehl et al. ............ 600/9 |
| 2005/0010265 A1 | 1/2005 | Fassio et al. |
| 2005/0033154 A1 | 2/2005 | deCharms |
| 2005/0038313 A1 | 2/2005 | Ardizzone |
| 2005/0046532 A1 | 3/2005 | Dodd |
| 2005/0107655 A1 | 5/2005 | Holzner |
| 2005/0113630 A1 | 5/2005 | Fox et al. |
| 2005/0124848 A1 | 6/2005 | Holzner |
| 2005/0148808 A1 | 7/2005 | Cameron et al. |
| 2005/0154426 A1 | 7/2005 | Boveja et al. |
| 2005/0182287 A1 | 8/2005 | Becker |
| 2005/0182288 A1 | 8/2005 | Zabara |
| 2005/0222625 A1 | 10/2005 | Laniado et al. |
| 2005/0234286 A1 | 10/2005 | Riehl et al. |
| 2005/0256539 A1 | 11/2005 | George et al. |
| 2006/0058853 A1 | 3/2006 | Bentwich |
| 2006/0094924 A1 | 5/2006 | Riehl |
| 2006/0106430 A1 | 5/2006 | Fowler et al. |
| 2006/0122454 A1 | 6/2006 | Riehl et al. |
| 2006/0122496 A1 | 6/2006 | George et al. |
| 2006/0149337 A1 | 7/2006 | John |
| 2006/0173274 A1 | 8/2006 | George et al. |
| 2006/0189866 A1 | 8/2006 | Thomas et al. |
| 2006/0199992 A1 | 9/2006 | Eisenberg et al. |
| 2006/0218790 A1 | 10/2006 | Day et al. |
| 2006/0287566 A1 | 12/2006 | Zangen et al. |
| 2007/0027353 A1 | 2/2007 | Ghiron et al. |
| 2007/0027504 A1 | 2/2007 | Barrett et al. |
| 2007/0083074 A1 | 4/2007 | Sotiriou |
| 2007/0100392 A1 | 5/2007 | Maschino et al. |
| 2007/0100398 A1 | 5/2007 | Sloan |
| 2007/0242406 A1 | 10/2007 | Annis et al. |
| 2007/0265489 A1 | 11/2007 | Fowler et al. |
| 2008/0200749 A1 | 8/2008 | Zheng et al. |
| 2009/0024021 A1 | 1/2009 | George et al. |
| 2009/0099405 A1 | 4/2009 | Schneider et al. |
| 2009/0099623 A1 | 4/2009 | Bentwich |
| 2009/0156884 A1 | 6/2009 | Schneider et al. |
| 2009/0187062 A1 | 7/2009 | Saitoh |
| 2009/0234243 A1 | 9/2009 | Schneider et al. |
| 2010/0004500 A1 | 1/2010 | Gliner et al. |
| 2010/0185042 A1 | 7/2010 | Schneider et al. |
| 2010/0256436 A1 | 10/2010 | Partsch et al. |
| 2010/0256438 A1 | 10/2010 | Mishelevich et al. |
| 2010/0256439 A1 | 10/2010 | Schneider et al. |
| 2010/0298623 A1 | 11/2010 | Mishelevich et al. |
| 2010/0331602 A1 | 12/2010 | Mishelevich et al. |
| 2011/0004450 A1 | 1/2011 | Mishelevich et al. |
| 2011/0082326 A1 | 4/2011 | Mishelevich et al. |
| 2011/0273251 A1 | 11/2011 | Mishelevich et al. |
| 2013/0096363 A1 | 4/2013 | Schneider et al. |
| 2013/0317281 A1 | 11/2013 | Schneider et al. |
| 2014/0200388 A1 | 7/2014 | Schneider et al. |
| 2015/0112118 A1 | 4/2015 | Mishelevich et al. |
| 2015/0133718 A1 | 5/2015 | Schneider et al. |
| 2016/0023015 A1 | 1/2016 | Schneider et al. |
| 2016/0067516 A1 | 3/2016 | Schneider et al. |
| 2016/0067518 A1 | 3/2016 | Mishelevich et al. |

FOREIGN PATENT DOCUMENTS

| | | |
|---|---|---|
| EP | 0709115 A1 | 5/1996 |
| EP | 0788813 A1 | 8/1997 |
| EP | 1326681 B1 | 1/2007 |
| GB | 2271931 A | 5/1994 |
| GB | 2336544 A | 10/1999 |
| JP | 64-046479 | 2/1989 |
| JP | 5-237197 | 9/1993 |
| JP | 2003-180649 | 7/2003 |
| JP | 2003-205040 | 7/2003 |
| KR | 10-0457104 | 11/2004 |
| WO | WO 98/56302 A1 | 12/1998 |
| WO | WO 99/39769 A1 | 8/1999 |
| WO | WO 99/55421 A2 | 11/1999 |
| WO | WO 00/74777 A1 | 12/2000 |
| WO | WO 00/78267 A2 | 12/2000 |
| WO | WO 02/09811 A1 | 2/2002 |
| WO | WO 02/32504 A2 | 4/2002 |
| WO | WO 03/082405 A1 | 10/2003 |
| WO | WO 2004/087255 A1 | 10/2004 |
| WO | WO 2005/000153 A2 | 1/2005 |

(56) References Cited

FOREIGN PATENT DOCUMENTS

| WO | WO 2006/124914 A2 | 11/2006 |
|----|-------------------|---------|
| WO | WO 2007/050592 A2 | 5/2007 |
| WO | WO 2007/130308 A2 | 11/2007 |

OTHER PUBLICATIONS

Avery et al.; A Controlled Study of Repetitive Transcranial Magnetic Stimulation in Medication-Resistant Major Depression; Biological Psychiatry; vol. 59; pp. 187-194; Jul. 2005.

Barker et al.; Non invasive magnetic stimulation of the human motor cortex; Lancet; vol. 1; pp. 1106-1110; May 1985.

Barker, A. T.; An introduction to the basic principles of magnetic nerve stimulation; Journal of Clinical Neurophysiology; vol. 8; No. 1; pp. 26-37; Jan. 1991.

Basser et al.; Stimulation of myelinated nerve axon by electromagnetic induction; Medical & Biological Engineering and Computing.; vol. 29; pp. 261-268; May 1991.

Bohning et al.; Mapping transcranial magnetic stimulation (TMS) fields in vivo with MRI; NeuroReport; vol. 8; No. 11; pp. 2535-2538; Jul. 28, 1997.

Conca et al.; Effect of chronic repetitive transcranial magnetic stimulation on regional cerebral blood flow and regional cerebral glucose uptake in drug treatment-resistant depressives. A brief report; Neuropsychobiology; vol. 45; No. 1; pp. 27-31; (Month Unavailable) 2002.

Dantec magnetic stimulation product information on MagPro X100 with MagOption; http://www.danica.nl/neuro/neuro-magnetische-stimulatoren.htm; Jan. 15, 2009.

Davey et al.; Designing transcranial magnetic stimulation systems; IEEE Transactions on Magnetics; vol. 41; No. 3; pp. 1142-1148; Mar. 2005.

Davey et al.; Modeling the effects of electrical conductivity of the head on the induced electrical field in the brain during magnetic stimulation; Clinical Neurophysiology; vol. 114; pp. 2204-2209; Jun. 2003.

Davey et al.; Prediction of magnetically induced electric fields in biologic tissue; IEEE Transactions on Biomedical Engineering; vol. 38; pp. 418-422; May 1991.

Davey et al.; Suppressing the surface field during transcranial magnetic stimulation; IEEE Transactions on Biomedical Engineering; vol. 53; No. 2; Feb. 2006; pp. 190-194.

DeRidder et al.; Transcranial magnetic stimulation for tinnitus: influence of tinnitus duration on stimulation parameter choice and maximal tinnitus suppression; Otol Neurotol.; vol. 26; No. 4; pp. 616-619; Jul. 2005.

Epstein et al.; Magnetic coil suppression of visual perception at an extracalcarine site; J. Clin. Neurophysiol; vol. 13; No. 3; pp. 247-252; May 1996.

George, Mark S.; Stimulating the brain; Scientific American; Sep. 2002; pp. 67-73.

Han et al.; Multichannel magnetic stimulation system design considering mutual couplings among the stimulation coils; IEEE Trans. on Biomedical Engineering; vol. 51; No. 5; pp. 812-817; May 2004.

Hayward et al.; The role of the anterior cingulate cortex in the counting stroop task; Exp Brain Res; vol. 154(3); pp. 355-358; Feb. 2004.

Hovey, C. et al.; The new guide to magnetic stimulation; The Magstim Company Ltd.; Carmarthenshire, United Kingdom; Oct. 2003.

Huang et al.; Theta Burst Stimulation of the Human Motor Cortex; Neuron; vol. 45; pp. 201-206; Jan. 2005.

Isenberg et al.; Low frequency rTMS stimulation of the right frontal cortex is as effective as high frequency rTMS stimulation of the left frontal cortex for antidepressant-free, treatment-resistant depressed patients; Ann Clin Psychiatry; vol. 17; No. 3; pp. 153-159; Jul.-Sep. 2005.

Lang et al.; How does transcranial DC stimulation of the primary motor cortex alter regional neuronal activity in the human brain?; Eur. J. Neurosci.; vol. 22; No. 2; pp. 495-504; Jul. 2005.

Lin et al.; Magnetic coil design considerations for functional magnetic stimulation; IEEE Trans. On Biomedical Eng.; vol. 47; No. 5; pp. 600-610; May 2000.

Magstim Website: http://www.magstim.com/magneticstimulators/magstimacc/12494.html (printed Mar. 23, 2010).

Martin et al.; Transcranial magnetic stimulation for treating depression; Cochrane Review; (Month Unavailable) 2002 (in (eds.): The Cochrane Library. Oxford: Update Software: The Cochrane Library. Oxford: Update Software.).

Mayberg et al.; Deep brain stimulation for treatment-resistant depression; Neuron; vol. 45; pp. 651-660; Mar. 2005.

Nadeem et al.; Computation of electric and magnetic stimulation in human head using the 3-D impedance method; IEEE Trans on Biomedical Eng; vol. 50; No. 7; pp. 900-907; Jul. 2003.

Ohnishi et al.; rCBF changes elicited by rTMS over DLPFC in humans; Suppl Clin Neurophysiol.; vol. 57: pp. 715-720; (Month Unavailable) 2004.

Roth et al.; A coil design for transcranial magnetic stimulation of adeep brain regions; J. Clin. Neurophysiology; vol. 19; No. 4; Aug. 2002; pp. 361-370.

Ruohonen et al.; Theory of Multichannel Magnetic Stimulation: Toward Functional Neuromuscular Rehabilitation; IEEE Transactions on biomedical Engineering; vol. 46; No. 6; pp. 646-651; Jun. 1999.

Ruohonen, J.; Transcranial magnetic stimulation: modelling and new techniques; (doctoral dissertation); Helsinki Univ. of Tech.; Dept. of Eng. Physics and Mathematics; Espoo, Finland; Dec. 1998.

Ruohonen et al.; (Chapter 2); Magnetic stimulation in clinical neurophysiology; Second Ed.; Ed. Elsevier Inc.; pp. 17-30; (Month Unavailable) 2005.

Ruohonen et al.; Focusing and targeting of magnetic brain stimulation using multiple coils; Medical & Biological Engineering and Computing; vol. 35; pp. 297-301; May 1998.

Sackheim, H. A.; Commentary: Magnetic stimulation therapy and ECT; Convulsive Therapy; vol. 10; No. 4; Dec. 1994; pp. 255-285.

Sekino et al.; Comparison of current distributions in electroconvulsive therapy and transcranial magnetic stimulation; J. of Applied Physics; vol. 91; No. 10; pp. 8730-8732; May 15, 2002.

Speer et al.; Opposite effects of high and low frequency rTMS on regional brain activity in depressed patients; Biol. Psychiatry; vol. 48; No. 12; pp. 1133-1141; Dec. 15, 2000.

Takano et al.; Short-term modulation of regional excitability and blood flow in human motor cortex following rapid-rate transcranial magnetic stimulation; Neuroimage; vol. 23; No. 3; pp. 849-859; Nov. 2004.

Traad, Monique; A Quantitative Positioning Device for Transcranial Magnetic Stimulation; Engineering in Medicine and Biology Society; 1990; Proceedings of the 12th Annual Intl Conf. of the IEEE; Philadelphia, PA; p. 2246; Nov. 1-4, 1990.

Ueno et al.; Localized stimulation of neural tissues in the brain by means of a paired configuration of time-varying magnetic fields; J. Appl. Phys.; vol. 64; No. 10; pp. 5862-5864; Nov. 15, 1988.

Vayssettes-Courchay et al.; Role of the nucleus tractus solitarii and the rostral depressive area in the sympatholytic effect of 8-hydroxy-2-(di-n-propylamino)tetralin in the cat; Eur. J. Pharmacol.; vol. 242; No. 1; pp. 37-45; Sep. 21, 1993.

Wagner et al.; Three-dimensional head model simulation of transcranial magnetic stimulation; IEEE Trans. on Biomedical Engineering; vol. 51; No. 9; pp. 1586-1598; Sep. 2004.

Wasserman et al.; Therapeutic application of repetitive magnetic stimulation: A review; Clinical Neurophysiology; vol. 112; pp. 1367-1377; Apr. 2001.

Wasserman, E. M.; Risk and safety of repetitive transcranial magnetic stimulation: report and suggested guidelines from the International Workshop on the Safety of Repetitive Transcranial Magnetic Stimulation, Jun. 5-7, 1996; Electro-encephalography and Clinical Neurophysiology; vol. 108; pp. 1-16; Jan. 1998.

Xiao et al.; Magnetic Nanocomposite Paste: An Ideal High- $\mu$, k and Q Nanomaterial for Embedded Inductors in High Frequency Elec-

(56) References Cited

OTHER PUBLICATIONS tronic Appls.; Proceedings of the 9th World Multiconference on Systemics, Cybernetics and Informatics; Orlando, FL; Jul. 10-13, 2005.

Mishelevich et al.; U.S. Appl. No. 12/680,912 "Transcranial magnetic stimulation with protection of magnet-adjacent structures," filed Mar. 31, 2010.

Schneider et al.; U.S. Appl. No. 12/838,299 entitled "Transcranial magnetic stimulation field shaping," filed Jul. 16, 2010.

Schneider et al.; U.S. Appl. No. 12/912,650 entitled "Sub-motor-threshold stimulation of deep brain targets using transcranial magnetic stimulation," filed Oct. 26, 2010.

Mishelevich et al.; U.S. Appl. No. 12/990,235 entitled "Transcranial magnetic stimulation by enhanced magnetic field perturbations," filed Oct. 29, 2010.

Schneider, M. Bret .; U.S. Appl. No. 13/169,967 entitled "Enhanced Spatial Summation for Deep-Brain Transcanial Magnetic Stimulation," filed Jun. 27, 2011.

Hsu et al., Analysis of Efficiency of Magnetic Stimulation; IEEE Transactions on Biomedical Engineering; vol. 50. No. 11; Sep. 2003; pp. 1276-1285.

Kamitani et al.; A model of magnetic stimulation of neocortical neurons; Neurocomputing; vol. 38; No. 40; Jun. 2001; pp. 697-703.

Kandel et al.; Chapter 12: Synaptic Integration; Principles of Neural Science; Editors: Kandel, Schwartz and Jessell; 4th Edition, McGraw-Hill; pp. 208-227; Jan. 5, 2000.

LeFaucheur, Jean-Pascal; Use of repetitive transcranial magnetic stimulation in pain relief; Expert Rev Neurother; vol. 8, No. 5: pp. 799-808; May 2008.

Miranda et al.; The Electric Field Induced in the Brain by Magnetic Stimulation: A 3-D Finite-Element Analysis of the Effects of Tissue Heterogeneity and Anisotropy; IEEE Transactions on Biomedical Engineering; vol. 50; No. 9; Sep. 2003; pp. 1074-1085.

Yu et al.; Pathogenesis of normal-appearing white matter damage in neuromyelitis optica: diffusion-tensor MR imaging; Radiology; vol. 246, No. 1: pp. 222-228; Jan. 2008.

Sadler, John W.; U.S. Appl. No. 13/512,496 entitled "Power Management in Transcranial Magnetic Stimulators," filed Sep. 17, 2012.

Schneider et al.; U.S. Appl. No. 13/586,640 entitled "Transcranial Magnet Stimulation of Deep Brain Targets," filed Aug. 15, 2012.

Alonso et al.; Right prefrontal repetitive transcranial magnetic stimulation in obsessive-compulsive disorder: a double-blind, placebo-controlled study; Am J Psychiatry; 158(7):1143-5; Jul. 2001.

Blount et al.; The Influence of Thyroid and Thiouracil on Mice Exposed to Roentgen Radiation; Science; 109(2822); pp. 83-84; Jan. 28, 1949.

Bodo et al.; The role of multidrug transporters in drug availability, metabolism and toxicity; Toxicol Lett; pp. 140-141; Review; pp. 133-143; Apr. 11, 2003.

Buxton; Pharmacokinetics and Phamacodynamics; Goodman & Gilman's The Pharmacological Basis of Therapeutics (11th Ed.); McGraw-Hill , © 2006; pp. 1-23; pub. date Oct. 28, 2005.

Cohen et al.; Repetitive transcranial magnetic stimulation of the right dorsolateral prefrontal cortex in posttraumatic stress disorder: a double-blind, placebo-controlled study; Am J Psychiatry; 161(3):515-24; Mar. 2004.

Fitzgerald et al.; Transcranial magnetic stimulation in the treatment of depression: a double-blind, placebo-controlled trial; Arch Gen Psychiatry; 60(10):1002-8; Oct. 2003.

Fregni et al.; Anodal transcranial direct current stimulation of prefrontal cortex enhances working memory; Exp Brain Res.; 166(1); pp. 23-30; Sep. 2005.

George et al.; Prefrontal Repetitive Transcranial Magnetic stimulation (rTMS) Changes Relative Perfusion Locally and Remotely; Human Psychopharmacol Clin Exp; 14(3); pp. 161-170; Apr. 1999.

Khedr et al.; Therapeutic effect of repetitive transcranial magnetic stimulation on motor function in Parkinson's disease patients; Eur J Neurol; 10(5):567-72; Sep. 2003.

Kimeldorf et al.; The effect of exercise upon the lethality of roentgen rays for rats; Science; 112(2902); pp. 175-176; Aug. 1950.

Lang et al.; Preconditioning with Transcranial Direct Current Stimulation Sensitizes the Motor Cortex to Rapid-Rate Transcranial Magnetic Stimulation and Controls the Direction of After-Effects; Biol. Psychiatry; 56(9): 634-639; Nov. 1, 2004.

Lemaire et al.; Influence of blood components on the tissue uptake indices of cyclosporin in rats; J Pharmacol Exp Ther; 244(2); pp. 740-743; Feb. 1988.

Li et al.; Antidepressant mechanism of add-on repetitive transcranial magnetic stimulation in medication-resistant depression using cerebral glucose metabolism; J Affect Disord; 127(1-3); pp. 219-229; Dec. 2010.

Mansur et al.; A sham stimulation-controlled trial of rTMS of the unaffected hemisphere in stroke patients; Neurology; 64(10):1802-4; May 24, 2005.

Nitsche et al.; Excitability changes induced in the human motor cortex by weak transcranial direct current stimulation; Journal of Physiology; 527(3):633-639; Sep. 15, 2000.

Rubin et al.; Radiosensitivity and radioresistance of tumors; Clinical Radiation Pathology; WB Saunder; Ch. 24, pp. 894-933; Jun. 1968.

Rubin et al.; The Modification of Radiation Response; Clinical Radiation Pathology; WB Saunders; Ch. 26, pp. 973-1008; Jun. 1968.

Smith et al.; Effect of thyroid hormone on radiation lethality; Am J Physiol; 165(3); pp. 639-650; Jun. 1951.

Theodore et al.; Transcranial magnetic stimulation for the treatment of seizures: a controlled study; Neurology; 59(4):560-2; Aug. 27, 2002.

Ueno; Individual differences in radio sensitivity of mice correlated with their metabolic rate; Acta Radiol Ther Phys Biol; 10(4); pp. 427-432; Aug. 1971.

Wasan et al.; Lipid transfer protein I facilitated transfer of cyclosporine from low- to high-density lipoproteins is only partially dependent on its cholesteryl ester transfer activity; J Pharmacol Exp Ther; 284 (2); pp. 599-605; Feb. 1998.

Zheng et al. High-frequency rTMS Treatment Increases Left Prefrontal Myo-Inositol in Young Patients with Treatment-Resistant Depression; Prog Neuropsychopharmacol Biol Psychiatry; 34(7); pp. 1189-1195; Oct. 1, 2010.

Schneider et al.; U.S. Appl. No. 13/808,806 entitled "Transcranial magnetic stimulation for altering susceptibility of tissue to pharmaceuticals and radiation," filed Apr. 23, 2013.

Schneider et al.; U.S. Appl. No. 13/877,428 entitled "Transverse transcranial magnetic stimulation coil placement for improved analgesia," filed Apr. 2, 2013.

Mishelevich et al.; U.S. Appl. No. 14/247,087 entitled "Shaped coils for transcranial magnetic stimulation," filed Apr. 7, 2014.

Schneider; U.S. Appl. No. 14/510,858 entitled "Treatment of degenerative brain disorders using transcranial magnetic stimulation," filed Oct. 9, 2014.

Alzheimer's Association; Changing the trajectory of alzheimer's disease: a national imperative; Washington, D.C.; May 19, 2010; retrieved from the internet on Nov. 13, 2014 (http://www.alz.org/documents_custom/trajectory.pdf).

Brainsway; Brainsway reports positive final results in alzheimer's trial; 2 pp.; Jan. 21, 2015; retrieved from the internet (http://www.evaluategroup.com/UniversalNiew.aspx?type=Story&id=357486).

Israel Hayom; Israel's neuronix offers new alzheimer's treatment; 2 pages; Nov. 5, 2012; retrieved from the internet (http://www.israelhayom/site/newsletter_article.php?id=6303).

Kessler et al.; Prevalence, severity, and comorbidity of 12-month DSM-IV disorders in the national comorbidity survey replication (NCS-R); Arch. Gen. Psychiatry; 62(6); pp. 617-627; Jun. 2005.

Samhsa (Center for Behavioral Health Statistics and Quality); National survey on drug use and health 2009 and 2010; 2010 Tables: Adult Mental Health; 80 pages; Nov. 14, 2014; retrieved from the internet (http://www.samhsa.gov/data/Nsduh/2k10MH_Findings/2k10MH_DTables/Sect1peMHtabs.htm#TopOfPage).

The International Consortium in Psychiatric Epidemiology (ICPE); Cross-national comparisons of the prevalences and correlates of

(56) References Cited

OTHER PUBLICATIONS mental disorders; Bull. World Health Organ.; 78(4); pp. 413-426; 2000 (year of pub. sufficiently earlier than effective US filed and any foreign priority date).

Bi et al; Synaptic modifications in cultured hippocampal neurons: dependence on spike timing, synaptic strength, and postsynaptic cell type; J. Neurosci.; 18(24); pp. 10464-10472; Dec. 15, 1998.

Dan et al.; Hebbian depression of isolated neuromuscular synapses in vitro; Science; 256(5063); pp. 1570-1573; Jun. 12, 1992.

Gahwiler et al.; Asynchronous pre- and postsynaptic activity induces associative long-term depression in area CA1 of the rat hippocampus in vitro; PNAS; 91(3); pp. 1148-1152; Feb. 1994.

Levy et al.; Temporal contiguity requirements for long-term associative potentiation/depression in the hippocampus; Neurocience; 8(4); pp. 791-797; Apr. 1983.

Lubke et al; Regulation of synaptic efficacy by coincidence of postsynaptic APS and EPSPs; Science; 275(5297); pp. 213-215; Jan. 1997.

Roth et al.; Safety and characterization of a novel multi-channel tms stimulator; Brain Stimul.; 7(2); pp. 194-205; Mar.-Apr. 2014.

\* cited by examiner

US 9,486,639 B2

TRAJECTORY-BASED DEEP-BRAIN STEREOTACTIC TRANSCRANIAL MAGNETIC STIMULATION

CROSS REFERENCE TO RELATED APPLICATION

This application is a continuation of U.S. patent application Ser. No. 11/429,504, titled "Trajectory-Based Deep-Brain Stereotactic Transcranial Magnetic Stimulation, filed on May 5, 2006. This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to systems for Stereotactic Transcranial Magnetic Stimulation of the brain to modulate neural activity at arbitrary deep and superficial brain locations.

BACKGROUND OF THE INVENTION

Transcranial Magnetic Stimulation (TMS) and Repetitive Transcranial Magnetic Stimulation (rTMS, a variant of TMS in which electromagnetic fields are produced in trains of multiple short pulses) have shown the ability to trigger neuronal firing in selected superficial brain regions. In at least one psychiatric condition (major depression), this effect of TMS and of rTMS appears to constitute an effective therapy. TMS and rTMS instrumentation are currently limited by their inability to focus their magnetic fields at depth. This is chiefly because a magnetic field always diminishes as a function its distance from the source.

Several techniques have been used to deliver stimulation to deep regions of the brain, as will be described. In the use of such technologies, MRI and other imaging techniques are useful for helping to ensure that the stimulation is directed to the correct brain structure. Methods for co-registering internal anatomy with medical instruments, and planning treatment with such medical devices are known in the art, and include methods provided in U.S. Pat. No. 5,207,223 (Adler), U.S. Pat. Nos. 5,891,034 and 6,236,875 (Bucholtz), and by U.S. Pat. Nos. 5,531,227 and 6,351,573 (Schneider). Such registration may be accomplished with the help of commercially available devices designed for surgical navigation, such devices including the Polaris system by Northern Digital (Waterloo, Ontario, Canada).

Magnetic stimulation of the brain and spinal cord has been known since the mid-1980's, Barker A T, Jalinous R, Freeston I L, "Non invasive magnetic stimulation of the human motor cortex" Lancet, 1985; 1:1106-110. A wide variety of clinical applications have been demonstrated, Wassermann, E. M., and S. H. Lisanby, "Therapeutic application of repetitive magnetic stimulation: a review," Clinical Neurophysiology, 112:1367-1377, 2001, with the major opportunity appearing to be in depression. Martin J L R, Barbanoj M J, Schlaepfer T E, Clots S P V, Kulisevsky J, A G (2002): Transcranial magnetic stimulation for treating depression (Cochrane Review). In (eds.): The Cochrane Library. Oxford: Update Software: The Cochrane Library. Oxford: Update Software.

Several patents and patent applications relate to such areas as electromagnetic coil design, simultaneous monitoring of EEG, simultaneous monitoring with functional MRI, and specific clinical applications. Among these are U.S. Pat. No, 6,179,771, Mueller, on coil arrangement U.S. Pat. No. 6,198,958, Ives and Pascual-Leone on monitoring of functional MRI during TMS U.S. Patent Application 20020007128 and U.S. Pat. No. 6,571,123, Ives and Pascual-Leone on monitoring of the EEG during TMS U.S. Patent Application 20040078056 and European Patent EP1326681, Zangen et al. on coil design U.S. Patent Application 2002007125, Davey on coil design U.S. Pat. No. 6,132,361, Epstein and Davey, coil design and clinical applications. Fox P, Lancaster J. Dodd S. Apparatus and Methods for Delivery of Transcranial Magnetic Stimulation. United States Patent Application U.S. 2003/0050527 A1 Fox P. Lancaster J. Apparatus and Methods for Delivery of Transcranial Magnetic Stimulation. United States Patent Application U.S. 2005/0113630 A1 Schneider M B, Mishelevich D J "Robotic Device for Providing Deep, Focused Transcranial Magnetic Stimulation". United States Patent Application U.S. 20050228209 A1.

While stimulation has shown promise in the treatment of depression, the limitation of the rTMS technique to the stimulation of only superficial structures has been a significant restriction. Depression itself has only been treatable because the superficial structures that are stimulated have neural connections to deep structures where the desirable effects actually occur. One way to increase the magnetic field delivered to depth would be increase the power input to the stimulating electromagnet. Unfortunately, simply increasing the output of the electromagnet is prevented from achieving the desired effect because of the proportional increase at the superficial location, where the field is much stronger to begin with. The resultant magnetic field could easily overwhelm the superficial structures and cause pain, unintended activation of non targeted structures, possibly seizures and neural excitotoxicity.

The general effect of transcranial magnetic stimulation is the depolarization of neural membranes and the resultant production of action potentials. Magnetic fields stimulate neural tissue because electrical current flow is induced. See Davey, K. R., C. H. Cheng, et at (1991). Prediction of magnetically induced electric fields in biologic tissue. IEEE Transactions on Biomedical Engineering 38: 418-422; Davey, K. R., C. M. Epstein, et al. (2004). Modeling the Effects of Electrical Conductivity of the Head on the Induced Electrical Field in the Brain During Magnetic Stimulation. Clinical Neurophysiology 114: 2204-2209.

When the flow of electrical charges in the intracellular and extracellular compartments is interrupted by a neural membrane, a differential voltage is generated across that membrane. The cell membrane is either depolarized or hyperpolarized depending on the direction of the current flow. That direction of the induced electrical-current flow is determined by the directionality of the magnetic field. The embodiments described herein utilize arrays of magnets arranged such that when the coils are simultaneously energized, individual vector components of the applied magnetic field can be, to a functional extent, spatially segregated. By "spatially segregated" it is meant that the arrangement of coils creates regions of enhanced field strength and regions of diminished field strength in the magnetic field in predetermined spatial locations.

Ruohonen, J., "Transcranial Magnetic Stimulation: Modeling and New Techniques" Ph.D. Dissertation in Engineering, Helsinki University of Technology, Espoo, Finland (52 pages), 1998 has presented a potential theoretical model for neural activation by magnetic fields inducing electrical currents. Five cases are described. Case 1: if the induced electrical field is uniform and parallel to the long axis of the axon, no polarization occurs. Case 2: if the magnetic field induces an electrical current with a gradient, the axon membrane has zones of depolarization and hyperpolarization. Case 3: even in the presence of a unithrm field, depolarization will occur at an axon bend. Case 4: transverse activation can produce depolarization and hyperpolarization on opposite sides of the axon. Case 5: depolarization occurs at neural terminations even in the presence of a uniform electrical field. Cases 3 and 5 likely represent the situation with the brain where the axons tend to be thin and curved while Case 4 is representative of the situation in peripheral nerves (e.g., the ulna nerve in the arm) where the nerves tend to be both longer and thicker. TMS is thought to impact axons rather than cell bodies.

There is some evidence that, when applied at rates of approximately one pulse per second or less, recipient nerves are inhibited, or down-regulated in their activity. At rates greater than one pulse per second, the result tends to be excitatory for affected neurons. Stimulating at too great a rate can cause seizures Wassermann, E. M., 1998) "Risk and safety of repetitive transcranial magnetic stimulation: report and suggested guidelines from the International Workshop on the Safety of Repetitive Transcranial Magnetic Stimulation, Jun. 5-7, 1996," Electroencephalography, and Clinical Neurophysiology, 108:1-16, 1998.

Because TMS apparatuses are physically large and bulky, and because their use at effective power levels is generally not comfortable, applying continuous stimulation over a period of hours, days or beyond is not practical. Still, a prolonged therapeutic effect of for example, in the case of depression (Martin et al., 2002) and tinnitus De Ridder D, Verstraeten E, Van der Kelen K, De Mulder G, Sunaert S, Verlooy J, Van de Heyning P, Moller A. Transcranial magnetic stimulation for tinnitus: influence of tinnitus duration on stimulation parameter choice and maximal tinnitus suppression. Otol Neurotol. 2005 July;26(4):616-9 most likely occur because of a re-training of pathways and activity levels.

Factors that influence the strength of neural stimulation depend on many factors including:

(a) Coil configuration—The majority of electromagnets used in clinical treatment are double coils, typically each coil having an outer diameter of 70 mm. The radial component of such an electromagnet is the direction that is geometrically normal (perpendicular) to the plane of the coil face;

(b) Coil size;
(c) Coil material;
(d) Pulse strength;
(e) Pulse shape;
(f) Pulse frequency;
(g) The electrical conductive properties and geometry of each specific area of anatomy receiving magnetic pulses; and
(h) The direction of the nerve or nerve tract receiving the generated electrical field in relation to the direction of the magnetic field at that point. (Ruohonen, 1998; Basser P J, Roth B J. Stimulation of myelinated nerve axon by electromagnetic induction. Med Biol Eng Comput. 29, 261-268. 1998; Fox et al. in U.S. Patent Applications 20050113630 and 20030050527).

Small coils (e.g., 20 to 30 mm in diameter) deliver energy with greater focus than their larger counterparts (Ruohonen, J. and R. J. Ilmoniemi, "Focusing and targeting of magnetic brain stimulation using multiple coils," Medical & Biological Engineering and Computing, 35:297-301, 1998; Han, B. Y., Chun, I. K., Lee, S. C., and S. Y. Lee, "Multichannel Magnetic Stimulation System Design Considering Mutual Couplings Among the Stimulation IEEE Transactions on Biomedical Engineering, 51:812-817, 2004, and Mueller, U.S. Pat. No. 6,179,771), Unfortunately, the smaller the coil, the less field strength it is able to generate at any given level of electrical input. Increasing the current vastly increases the cooling needs of the magnets. Because of the rapid rate of magnetic field strength fall of with distance from the coil, and the difficulty in providing efficient cooling mean, highly focal coils tend to have little ability to penetrate to depth. For a given magnet, for distances that are small relative to the radius of the magnet's coils, the fall off of magnetic field is a property of the magnet itself. For distances that are large relative to the size of the magnet, the fall-off is one over the distance cubed. This factor limits the ability for the magnetic fields of small coils to penetrate to depth. It should be emphasized that for none of the multi-coil arrays described in the cited literature was delivery to depth an objective, nor would they have been capable of that effect, even with adequate power and cooling, given the obtuse angle of their field confluence, their low power, and melting that uncooled coils of that size and configuration would have undergone at high power delivery. In fact, Ruohonen, et al. state that focusing at depth is not possible, reasoning that the discordance between the location of a magnetic field maxima and an electric field maxima may be displaced (an effect that may be compensated for as described by herein by the inventors), and that the magnetic field entering a head has no radial component (an effect of limited significance if true, and also contested by researchers including Wagner, et al, cited below).

The Hesed coil (Zangen et al., U.S. Patent Application 20040078056 and European Patent EP1326681) was developed in order to more efficiently deliver magnetic field to depth. As a result of its design, the fall-off rate for magnetic field strength over distance is less steep than fbr conventional TMS coils. However this improved depth penetration is achieved with an overall decline in locality when compared with conventional coils. When a magnetic field is applied in the manner described in these references, the intensity of the magnetic field at depth is always less than that at the surface.

The most focal means used today for providing brain stimulation at depth is by use of current-pulsed surgically implanted electrodes, also known as deep-brain stimulation "DBS". Used for the treatment of conditions such as Parkinson's Disease, DBS also hold promise for the treatment of many neurological and psychiatric disorders, due to its ability to selectively activate and inactivate precise regions of the brain. Unfortunately, DBS necessarily involves an invasive neurosurgical procedure, which is expensive, and fraught with medical risks including intracranial bleeding and infection.

It would be desirable to non-invasively achieve the benefits of DBS by directing electromagnetic energy into deep structures without overwhelming superficial structures. It has been proposed in commentary to simultaneously use multiple coils to summate in deep structures (Sackheim H A. Magnetic Stimulation Therapy and ECT (Commentary). Convulsive Therapy 1994; 10(4); 255-8). Work by Bohning and George (Bohning D E, Pecheny A P, Epstein C M, Speer A M, Vincent D J; Dannels W; George M S Mapping transcranial magnetic stimulation (TMS) fields in vivo with MRI. NeuroReport Volume 8(11), 28 Jul. 1997, p 2535-2538) illustrated the reinforcing effect of simultaneously applied magnetic fields. Two pulsed magnetic fields were delivered at an unspecified acute angle from opposite sides of the temples. The resultant magnetic fields were demonstrated to have a reinfbrcing effect such that the magnetic field demonstrated to be higher at the midline of the brain than it would have had only a single magnet been present. However, this work did not produce or teach a magnetic coil configuration that would enable the intensity at depths to exceed that on the surface, and no further efforts at improving the process were documented.

Fox, et al., (U.S. Patent Applications US 2003/0050527 A1, and U.S. Patent Application US 2005/0113630 A1) propose means for positioning a TMS coil so as to have a maximal biological effect to nerve tissue. This method is based on the use of a single coil targeting a point on the superficial cortex of the brain, and does not discuss the use of multi-coil arrays or concentrating energy at depth.

An alternative approach to non-invasively providing deep brain stimulation using magnetic coils is provided by the inventors of the present invention in Schneider M. B, and D. J. Mishelevich, U.S. Patent Application US 20050228209 A1.

Prior works known by Applicant fall short of configuring coil arrays so as to produce a specific biological effect at a specific locus deep in the brain without significantly impacting superficial structures.

A method for non-invasively modulating the activity of neural tissue at depth at selectable arbitrary locations with the human body, without overwhelming superficial neural structures, would provide significant medical benefits. Additional objects and advantages sought to be achieved by various ones of the methods and systems disclosed herein include:

(a) to provide a system allowing the user to concentrate more magnetic field at depth than at superficial locations that are closer to the stimulating electromagnets, thereby reducing discomfort as well as the risks of seizure and excitotoxicity.

(b) to provide a system that is both non-invasive and more cost effective than implanted Deep Brain Stimulation with electrodes, (c) to provide a method by which the aim of a neuromodulation device such as that described herein may be offset from the target structure in order to compensate for predicted or observed magnetic/electric field discordance, (d) to give easy access to a wide variety of neural targets at depth, thereby greatly increasing the breadth of conditions that can be treated such as chronic pain, Alzheimer's Disease, obsessive compulsive disorder, addictions, obesity, Parkinson's Disease and other conditions, (e) to provide a more effective treatment of depression, which while it can currently be treated with conventional rTMS, could be treated more effectively by direct impact on targets instead of using indirect pathways as is done with prior art methods.

DETAILED DESCRIPTION

The present application describes a system and method for stereotactic transcranial magnetic stimulation or modulation ("sTMS"). The disclosed system and method uses an array of coils arranged in a predetermined configuration and pulsed substantially simultaneously so that at select spatial vectors, the magnetic field strength at a deep target exceeds that on the surface, close to the coils.

The disclosed method derives its effect, in part, by recognizing that in addition to considering total magnetic field strength at a given location, consideration of the strength and direction of individual X, Y, and Z magnetic vectors from an array of coils allows an arrangement of the coils to be selected such that the magnetic fields of the magnets will combine in a manner that intensifies some areas of the overall magnetic field and weakens others. In the appropriate configuration, the magnetic field along a given axis (say, for the purposes of one example, the Z-Axis defined as a radial component of energy emitted from a reference one of the coils) is augmented because when the pulsed fields from simultaneously stimulated electromagnets are combined, the field along the Z-axis is emphasized, and the net magnetic stimulation at the target at depth is greater than at superficial locations when the Z axis (radial component) of the reference magnet is directed towards the target. Such greater stimulation at depth than superficial locations avoids undesirable side effects such as seizures. This allows for the selection of a magnet array that will produce a magnetic field having an area of specific influence (i.e. one having an intensity and direction sufficient to cause a desired neurological effect) located at a select deep brain structure.

In any applicable configuration, the magnetic fields from coils in the given array are combined to generate a field having an area of specific influence at the target structure. The pulsed magnetic field over the area of specific influence induces the flow of electrical current in the target neural structure, causing the electrical potential across neural membranes to be altered. If the resultant depolarization exceeds threshold an action potential will be generated.

The principles described herein are not specific to any one coil design or composition (e.g., the coil shape or whether the coils have an iron core or not) as long as the chosen array generates a magnetic field profile that will produce an area of specific influence at the desired location. The coil array can be stationary or moved during stimulation, and additional coils can be added to the array in order to augment its function. In the appropriate applications, stimulating at depth using the Deep Brain Stimulation/Modulation techniques described herein could provide significant health benefits.

Figure 1A:
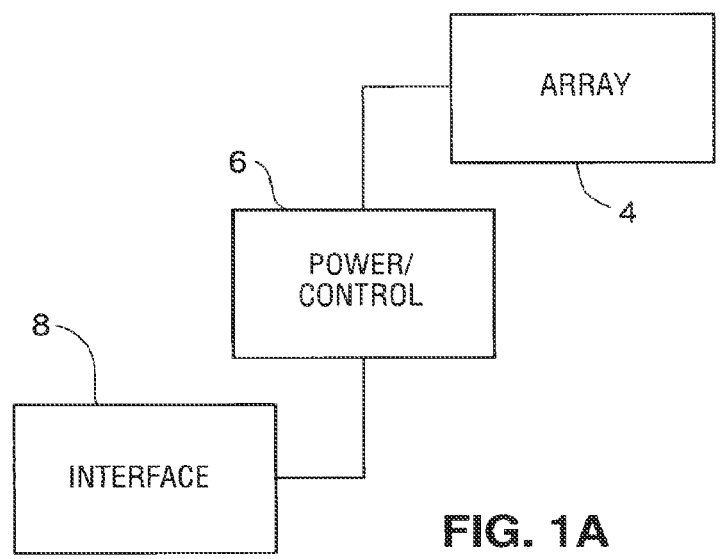
FIG. 1A is a simplified block diagram of a neuromodulation system using principles described herein.

FIG. 1A is a simplified block diagram of a neuromodulation system 2 of a type suitable for use with the methods and magnetic arrays described herein. System 2 includes a magnetic array 4, a power and control system 6, and a user interface 8 which may include one or more input devices (e.g. keyboard, mouse, touch screen, foot pedal) allowing a user to select stimulation parameters and initiate a treatment sequence.

Various power and control systems 6 may be used with the disclosed embodiments. One suitable power and control system 6 is the Magstim SuperRapid (Magstim, LTD, Wales, U.K.) power system and controller under the custom control software application running on an associated computer. Power is set in accordance with computations of the power necessary to exert the desired effect at the selected brain location.

Figure 5:
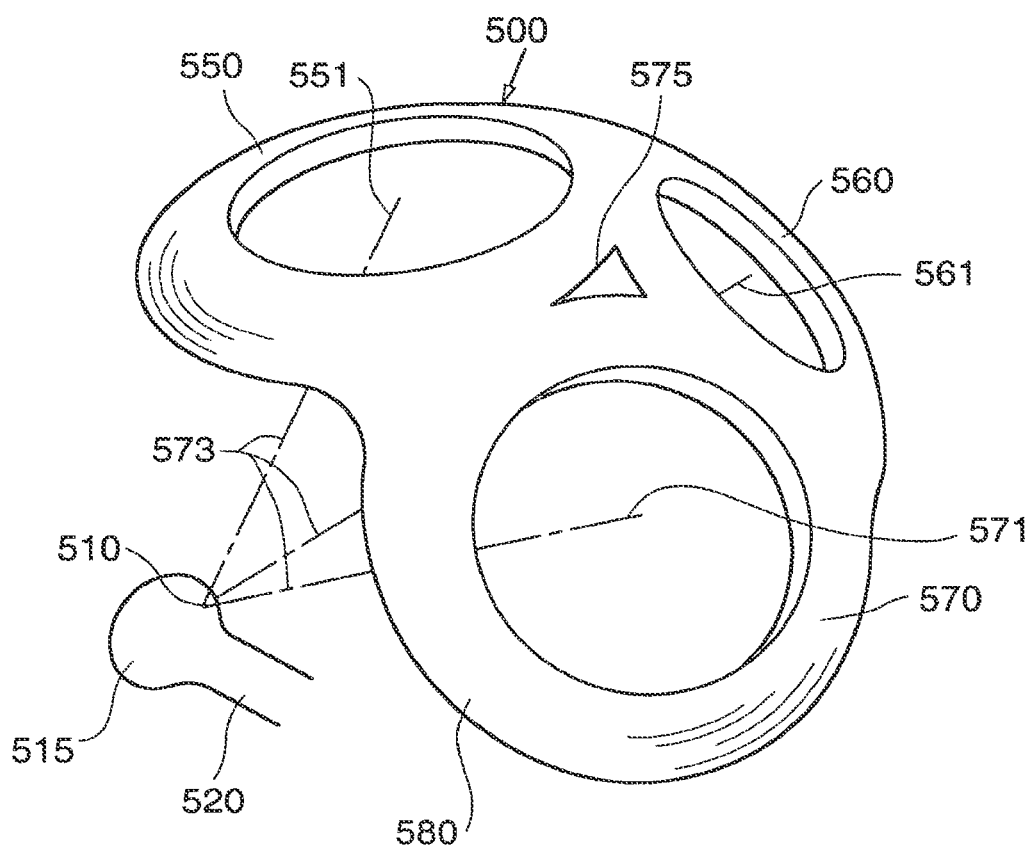
FIG. 5 is a perspective view of yet another alternative magnet array.

The array 4 may be equipped with electromagnets such as the Magstim double coil (outer diameter of each coil is 70 mm) electromagnet (Part Number 9925-00), or equivalent magnets to produce the magnetic fields. Double-coils (including figure-eight and butterfly coil configurations) produce a focused magnetic field at the intersection of the two circles of the figure-eight and may be preferable fir use in practicing the disclosed methods. Alternative coils may instead be used, some of which are described in connection with FIG. 5. The direction of the current for a given electromagnet can be reversed, if necessary.

Figure 1B:
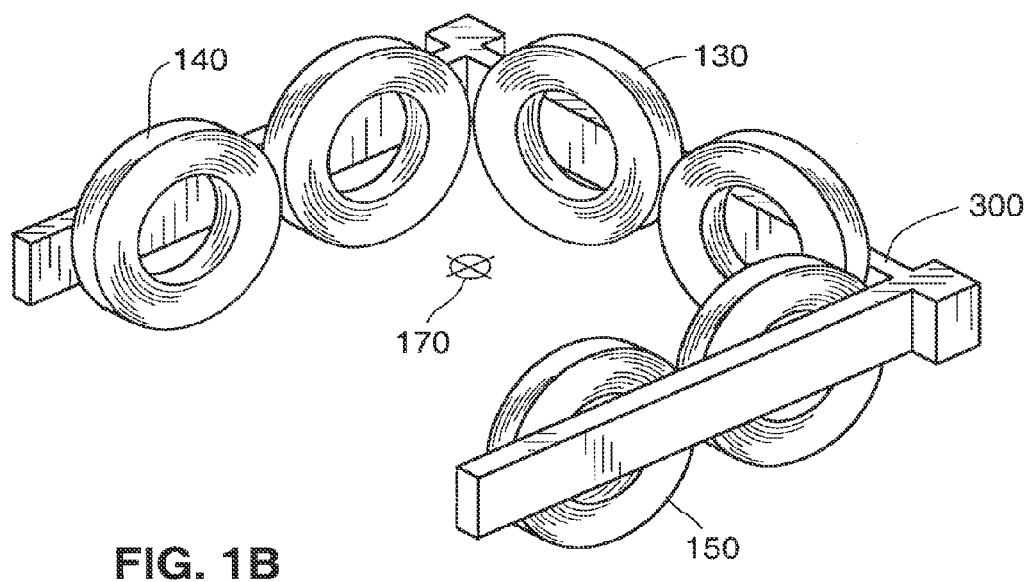
FIG. 1B shows a three-electromagnetic coil embodiment in perspective with a sample target.

A preferred magnet array includes three double-coil electromagnets at 0, 90, and 180 degrees on a circular or oval frame aimed inwards towards the designated target with additional coils possible. For example, FIG. 1B shows an embodiment with three electromagnetic coils shown in perspective. The coils 130, 140, 150 are held in a frame 300. A support (not shown) is used to maintain the frame in the desired position relative to the head of the patient. The frame 300 will generally be positioned with the coils surrounding a portion of the patient's head.

Figure 1C:
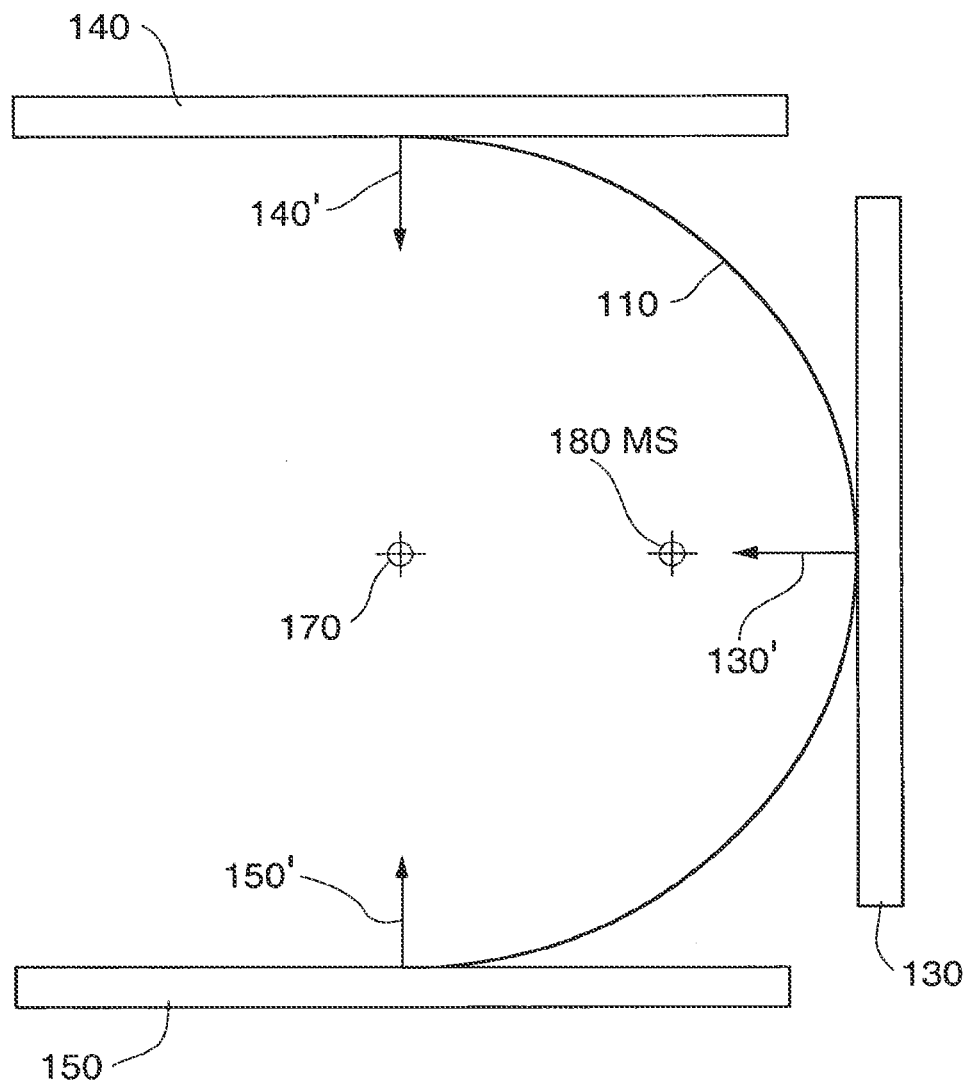
FIG. 1C shows a plan view of the configuration of the array of three magnets shown in FIG. 1A, illustrating the magnets mounted to an alternative frame.

FIG. 1C, which is a view from above, shows the electromagnets 130, 140, 150 held orthogonally in an array mounted on frame 110. In this embodiment, frame 110 is a circular or oval frame aimed inwards towards the target. Electromagnet 130, with its center aimed in radially from the 90-degree position, is a double-coil, typically 70 mm in diameter each, but is not restricted to this dimension. The frame is oriented such that the target 170 to be stimulated is located where radial components of the electromagnets intersect. Target 170 is an identified three-dimensional area of the brain of a patient whose head is disposed within the frame. In the FIGS. 1B and 1C embodiment, the radial components 130', 140', 150' selected to intersect at the target 170 correspond to the geometric centers of the electromagnetics 130, 140, 150. In other words, in this embodiment the radial component 130' of electromagnet 130 is the radial component where the two coils of the electromagnet come together and corresponds to the region where the field strength from the electromagnet 130 is highest at any given distance from the electromagnet 130 (see the field strength lines 190 shown in FIG. 2). In other embodiments, the intersecting radial component from a particular electromagnet may or may not correspond to the region of highest field strength for that magnet or the geometric center of that electromagnet.

Electromagnet 130 is termed the "reference magnet," and the radial component 130' of its magnetic field is designated as the Z axis for the purposes of this description, In FIG. 1C, this Z axis is coincident with the Z axis of the overall coordinate system in which the Z axis extends horizontally on the page, the X axis runs vertically on the page, and the Y axis is oriented perpendicular to the plane of the page. In the preferred embodiment, electromagnets 140 and 150 (which are also preferably double-coil electromagnets) have their centers aimed in radially from the 0- and 180-degree positions, i.e. such that the radial axes 130', 140', 150' of the electromagnets 130, 140, 150 are separated by 90°. in this embodiment, the target position 170 is in the plane in which the center axes of electromagnets, 130, 140, 150, are located. A representative superficial location is position 180 (also designated as MS for Middle Superficial), considering the nose of the patient pointed north to the 0-degree position).

As discussed, the system described herein arranges the magnets such that radial components from the magnets meet at deep target structures, thus allowing the system to direct a higher magnetic field at deep target structures (e.g. target 170) than at superficial positions (e.g. structure 180). According to the disclosed embodiments, ratios of Z-Axis magnetic field at the target versus superficial locations typically fall within a range of 1.5:1 to 8.5:1.

Figure 2:
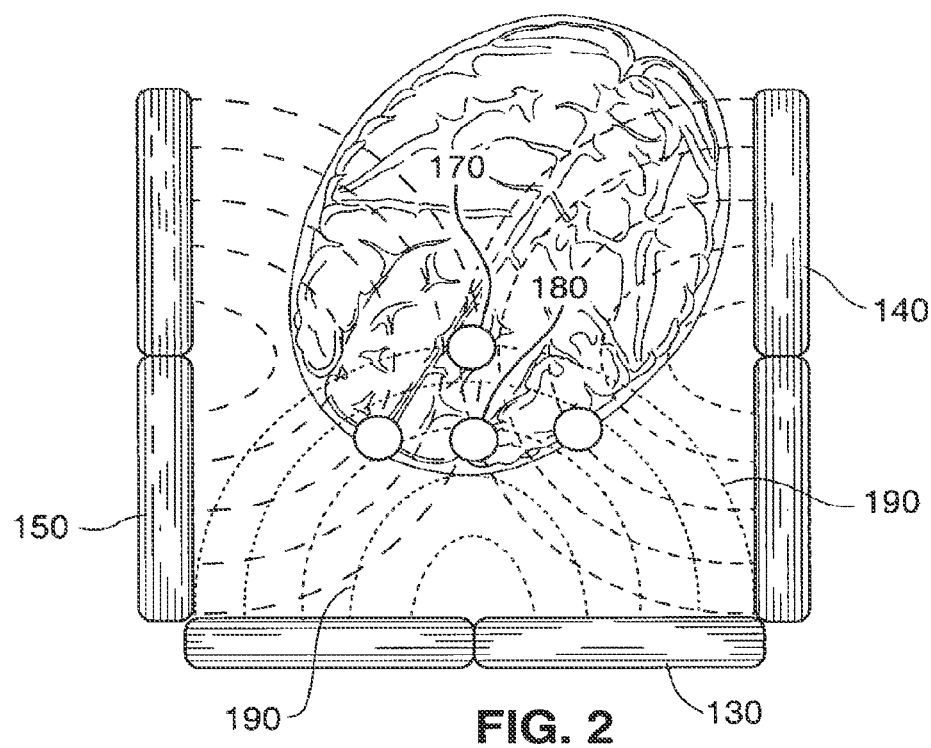
FIG. 2 shows a cross-sectional. top view of a head and bran and schematically illustrates magnetic energy patterns from the coil arrangement of FIGS. 1B and 1C.

The inventors of the disclosed system believe that when magnetic energy from a TMS coil is directed into a patient's head, a substantial radial component (along with other vector components) of the energy will penetrate the skull, meninges, and their associated surface charges. This is supported by recent work by authors such as Wagner (Wagner T A, Zahn M, Grodzinsky A J, Pascual-Leone A; Three-Dimensional Head Model Simulation of Transcranial Magnetic Stimulation. IEEE Transactions on Biomedical Engineering. Vol. 51, NO. 9, September 2004. 1586-1598). Coil arrangements according to the disclosed system and method are selected such that the Z-axis magnetic field generated by the reference coil 130 makes the primary contribution needed to achieve the desired effect in the target structure. Energy emitted from the coils 140, 150 contribute to the effectiveness of the Z-axis field by shaping the field of the reference coil 130. Specifically, it is believed that the magnetic fields generated by the coils 140, 150 cancel lateral portions of the magnetic field produced by reference coil 130, allowing the radial component 130' of the reference coil's field (i.e. the portion lying along the z-axis), to be of optimal strength for stimulation. The energy emitted by coils 140, 150 also contributes to the Z axis energy; but those effects are small relative to the Z axis energy from the reference coil. Thus, as best shown in FIG. 2, energization of the coils 130, 140, 150 will produce a magnetic field concentrated at the target 170, while the coils 140, 150 will diminish the magnetic field of the reference coil at locations offset from the vector 130'.

Although the FIG. 1B embodiment shows a Z-axis component as being the primary component fbr stimulation, in one alternative embodiment, a magnetic field having a radial component along an axis other than the Z axis may be the one directed towards and having the most impact on the target. Moreover, although the FIG. 1B embodiment shows an array in which the radial component of coils 140, 150 are offset from the radial component of coil 130 by approximately 90°, alternative angular offsets may be used, including but not limited to angles of 45°. In another alternative embodiment, coils 130 and 140 might be separated from one other by an angle that differs from the angle separating coils 130 and 150.

Figure 3:
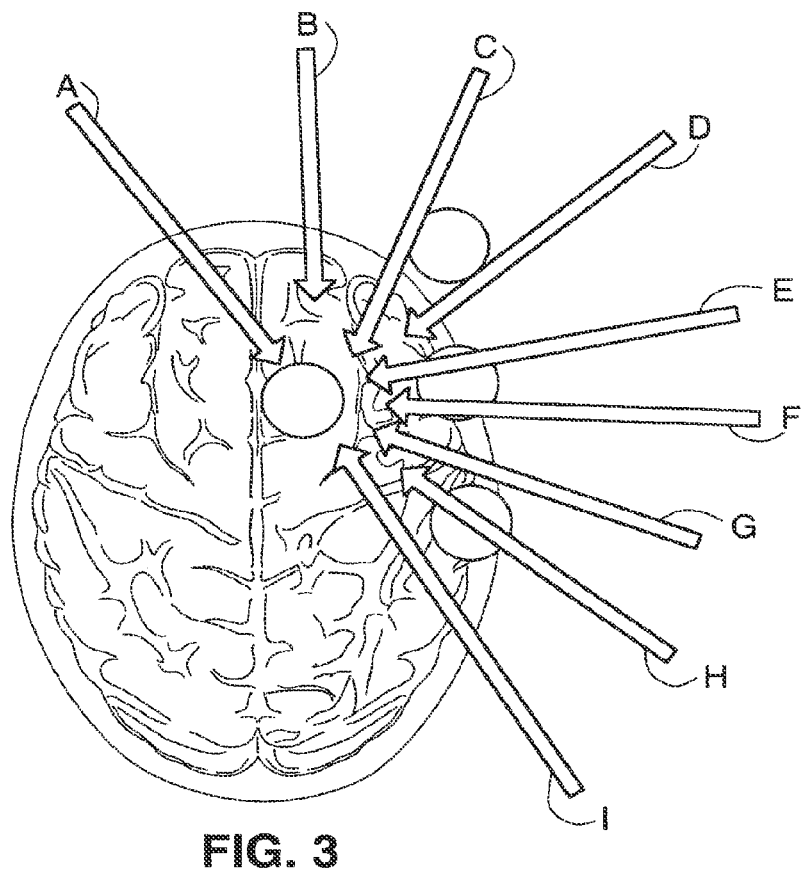
FIG. 3 shows a cross-sectional top view of a head and brain and schematically illustrates a number of radial components of magnetic fields emitted from hypothetical magnetic coils positioned at a variety of locations.

Thus, referring to FIG. 3, while a preferred combination of coils might include radial components along axes designated A, E and I, other suitable combinations of magnets might be employed having radial components along other combinations of the axes, including select ones of the illustrated axes A through I. In any case, it is most desirable to select magnet arrays that will generate higher electric fields at the target than at superficial structures. More arbitrary positioning of electromagnets can inhibit the desired enhancing of the field at the target depth. For example, while an array of coils producing radial components along axes A, E and I in FIG. 3 might give beneficial results, stimulating with radial components along axes A, E and I in combination with radial components along other ones of the illustrated axes can produce a Z-axis field strength that is significantly lower than that produced when only the A, E and I axis coils are energized.

In another alternative embodiment, the electromagnets in the array are oriented and pulsed such that the magnetic-field vector with the greatest impact is one comprised of magnetic fields emitted by coils oriented with their radial components positioned along a suitable combination of axes. In other words, the vector having the greatest impact need not necessarily coincide with a radial component of one of the electromagnets but may be transverse to the radial components of all of the electromagnets.

The FIG. 1B array uses an array of three electromagnetics, whereas in other embodiments additional electromagnets might be added at suitable angles selected to produce depolarization at the target deep tissue sight. Such embodiments may include configurations where the electromagnets are not placed at equal angles of separation. The selected combination of radial components may or may not lie within a single plane.

Figure 4:
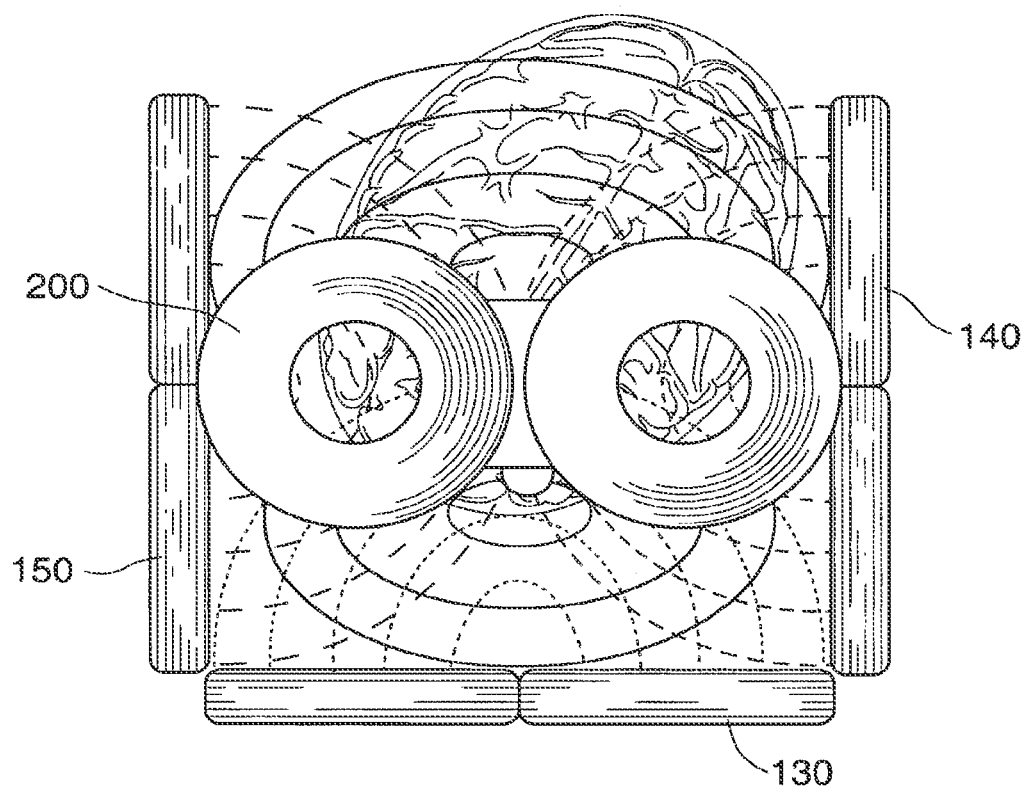
FIG. 4 shows a plan view of an alternative array using four magnets.

For example, referring to FIG. 4, a coil array as shown in FIG. 1 may be supplemented by a fourth coil 200 facing in toward the intersection of those three coils 130, 140, 150 having radial components on the same plane. In such a case, the radial component of the magnetic field from the fourth coil intensifies the strength of the magnetic field where the vectors from the coils 130, 140, 150 converge. The coil 200 is energized either simultaneously with the other coils or it is energized sequential with energization of the coils 130, 140, 150 such that the field vectors combine with that of the other coils in the manner desired. In such an embodiment, the three coils 130, 140, 150 in the single plane might be oriented along the sides of a patient's head, while the fourth coil 200 might be on top of patient's head, pointing downward.

Although the figures show arrays in which electromagnets are of the same type, the electromagnets in the array need not be the same type. For example, the coils 130, 140 of FIG. 1B might differ in size, or one might be a figure-eight type of coil and the other might be a butterfly coil. Moreover, in any of the described embodiments, the absolute size and/or number of electromagnets is selected such that the size of the electromagnets relative to the distance to the target and the orientation of the electromagnets included in the array are such that the resulting effect at the target depth is augmented rather than diminished.

The array is preferably positioned relative to the target so as to achieve optimal access to the target and so as to aim energy towards the target in a manner that avoids delivery of large overall or vector component field strengths to structures that are not to be stimulated target structures. Accordingly, while the internal angular relationships (e.g. in the FIG. 1B example the 0-, 90-, and 180-degree positions of the electromagnets 130, 140, 150) are preferably fixed with respect to one another, the array itself may be placed in a variety of positions so as to meet the needs of the particular application. During use the array is thus positioned such that current will be induced in the neural structure of interest so action potentials will be fired to get the desired immediate effect, short-term effect, or long-term training effect. For example, referring again to FIG. 1C, to direct the enhanced vector 130' to an off-center target, one can position the coil array off-center with respect to the head and/or tilt it at a suitable angle to appropriately stimulate the target. In addition, there may be other local maxima and minima of the magnetic field that can be usefully employed.

In some alternative embodiments, more than one anatomical location may be simultaneously targeted. An example of this would include the situation in which one location is the primary target and one or more other locations are connected neural pathways which can have a secondary effect upon the primary target. If the secondary target causes a reaction which indirectly augments the intended effect upon the primary target, the intended neuromodulation effect is thereby enhanced.

The three-dimensional position of the target may be determined using known methods, such as by mapping coordinates from imaging and brain atlases as well as functional MRI and demonstrated activation with the TMS. Such methods are known and used in the art in connection with TMS and radiosurgical procedures. The positioning of the array relative to the patient need not be carried out manually. For example, one can use robotic position devices as discussed by Fox et al. in U.S. Patent Applications 20050113630 and 20030050527.

Examples of conditions that may be treated with the disclosed system, as well as brain structures that may be targeted for treating those conditions, include:

Parkinson's Disease: subthalamic Nucleus, globus pallidus extema

Depression: Anterior cingulate gyrus, posterior cingulate gyrus, suhgeniculate cingulate gyrus.

Chronic Pain: Anterior cingulate, dorsal cingulate gyrus, motor cortex

Obesity: Ventromedial nucleus of thalamus, Ventrolateral nucleus of thalamus

Obsessive Compulsive Disorder: Anterior limb of the internal capsule, subthalamic nuclei Addiction: Nucleus: accumbens, septum Alzheimer's Disease: hippocampus, posterior cingulate gyrus In an alternative embodiment shown in FIG. 5, coil array 500 is comprised of coils 550, 560, and 570. Each coil includes concentric loops of insulated conductive material (580). In this example each of these coils is of approximately equal size and shape, and the difference in their appearance in the figure is due to the perspective view. Importantly, this coil array represents an optimized compromise between four design parameters that frequently conflict with one another:

(a) First, coils 550, 560, and 570, within array 500, are each oriented so that the normal (radial) component (551, 561, 571) of the energy that they deliver points toward a single common convergence point 510, located at a substantial distance below array 500. Convergence point 510 has a predetermined spatial relationship to the intended target. In the embodiment shown wherein the array is composed of single rather than double coils, the convergence point will have a lower level of total energy than will areas lateral to the convergence point. Hence, placing the convergence point lateral to the intended target may be preferable, depending upon the desired effect and the specific nature of the surrounding anatomy. The target may be an axonal structure 520 or a grey matter structure 515 alone, without proximity to the other, or it may be at the junction of the two;

(b) Second, conforrnality of the array to the surface of the body (e.g. head) over which it is applied, minimizes energy loss within space outside the body;

(c) Third, maximization of the radius dimensions of each coil loop maximizes magnetic field power delivery;

(d) And finally, minimization of the coil array 500 overall size, so as to be able to position the array 500 on the body (e.g. head) of a patient minimizes the chance of stimulating sensitive non-target structures, even as the intended target is stimulated.

In order to accomplish this optimization, compromises made include minimizing the size of intracoil space 575, and a distortion of the shape of coils 550, 560 and 570 from pure circular forms into a shape in which the component loops have a somewhat triangular configuration. In such an embodiment, local minima and maxima in magnetic field strength are achieved in terms of specific vector components of the total field, as was demonstrated with the 90 degree array embodiment of FIG. 1B.

For each embodiment, stimulation parameters (e.g. pulse rate, pulse width and power) are determined based on the stimulation dose needed at the target. Stimulation dose may be derived as a predetermined percentage of the patient's resting motor threshold as determined (using known techniques) by delivering stimulation pulses over a determined region of the motor cortex and determining the power level at which visible movement of the corresponding part of the body (e.g. the right thumb) occurs. Typically the stimulation dose is in the range of 100-120% of the measured motor threshold for reaching a superficial cortical structure. To reach a deeper structure, a dose that is higher relative to the motor threshold is used to compensate for the fall-off of the energy field as it moves away from the source. The selected dose may also take into account the energy distribution produced by the array, and the pulse rate and duration. If stimulation is undesired, a dose below the stimulation threshold will be used. The individual vector components at points more superficial than he target at depth will be preferably maintained below the motor threshold.

In some cases, the stimulating magnetic field at the target is augmented by additional input stimulation coming from neural pathways that themselves are being stimulated by superficial neural-tissue stations that have been triggered by superficial magnetic-field stimulation.

In the selected array, all coils need not be driven with the same amount of power or direction of current, as long as the combined magnetic field is appropriate for the target depth and desired effect. Similarly, the pattern and/or frequency of pulses may also not necessarily be the same for each electromagnet in the configuration.

The system may employ a pulse pattern that is constant over the treatment duration or one in which the pattern of the magnetic-field pulses is interrupted at various points and intervals of time. This latter approach, for example, might be useful for protecting sensitive neural structures placed in the stimulation path between an electromagnet coil and the target.

A likely target position will be at the bend of an axon bundle (Ruohonen, 1998). The total magnetic field is not the most pertinent measure of predicted effect, because the directionality is critical to the induction of electrical current and thus the triggering of neural action potentials. Power levels to the magnets are set to a level that will obtain the desired effect without overwhelming superficial structures with resultant side effects such as a seizure. A software model for accomplishing this has been developed and is described herein.

Magnetic fields affect neurons by virtue of their ability to transform into an electric field within the aqueous medial surrounding neurons, and within the neural membranes themselves. The propensity for a magnetic field to transform into an electric field is controlled by factors such as the electrical conductivity of the media, and the local geometry within the anatomy. For this reason, the point of peak electric field within a human head may be spatially displaced from the point of maximal magnetic field. Consequently, it is a further object of the disclosed systems to provide a method by which the aim of a neuromodulation device such as that described herein may be offset, compensated for, re-aimed, or re-calibrated, so as to compensate for predicted or observed magnetic/electric field maxima displacement. For example, if the target structure lies within a region of lower conductivity than a non-target region immediately next to it, at least three offset strategies may be employed.

According to a first off-set strategy, the calculated magnetic field is moved so as to minimize the field strength at the highly conductive non-target, and to better maximize it at the less conductive target region. This may be accomplished in several ways, including (a) physical movement of the entire coil array, for example with a robot; and/or (b) changing the relative power between the various coils in the array so as to shift the field profile.

In a second off-set strategy, the calculated magnetic field is moved using the methods described in the previous paragraph so as to displace the "target" to a region of high conductivity that connects to the original target.

In a third exemplary off-set strategy, the overall power output of the coils is changed so as to increase the electric field at the target sufficiently, keeping in mind that the greater electric field at the non-target site will also be increased.

MRI imaging, for example, diffusion tensor imaging methods, may be particularly useful for inferring conductivity as well as geometry of biological tissue. In this manner the "highways" of high conductivity—basically the aqueous media surrounding nerve bundles—may be identified such that electric field within these highly conductive regions may be efficiently transferred to targeted regions of lesser conductivity. This process may be compared with pins on an IC chip receiving signals via current remotely applied to traces on a printed circuit board. Models of electric field generation have been developed, for example, by Wagner (Wagner, et al. 2004), which predict the amount propensity of tissue at given locations to generate and propagate electric field and can be used as the basis for such offset calculations.

Figure 6:
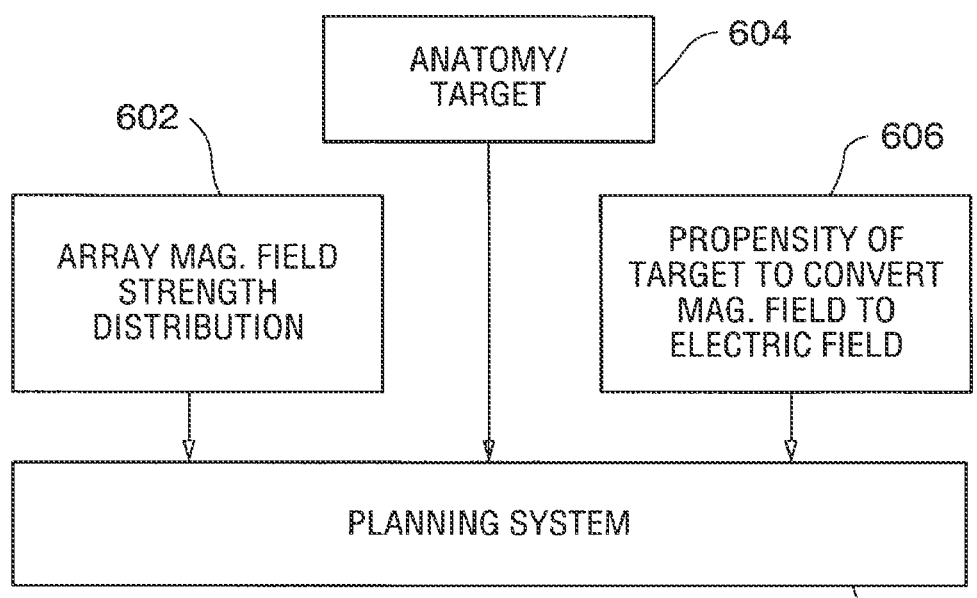
FIG. 6 schematically illustrates a planning system useful for determining stimulation parameters.

Accordingly, a target planning system 600 (FIG. 6) including a graphical user interface can be utilized in the treatment-planning phase to flag magnetic/electric field displacements, as they bear upon designated targets, and non-targeted critical structures. Such an interface may contain a tool with which to correct for this displacement, in consideration of projected consequences of that displacement. In one embodiment such treatment-planning system and software represented schematically in FIG. 6 includes means to coordinate two, three or more spatially representative data sets: (a) one data set 602 representing the calculated magnetic field strength distribution generated by the array, (h) another data set 604 representing the pertinent anatomy, including the target (for example, a 3-dimensional standard structural or a "functional" image such as PET or fMRI which shows the metabolic activity of various regions). Another exemplar (c) (labeled 606) represents the propensity of the target to convert magnetic field into electric field.

This data set may be derived, for example, from a diffusion tensor MR image, or from maps obtained constructed from a composite of sources (e.g., Wagner, et al 2004). In some cases, data sets (b) and (c) can be effectively represented by a single data set, such as a diffusion tensor MR image.

By registering the data sets 602, 604, 606 onto a single coordinate system visual representations of the data sets may be displayed using the graphical output. Methods for moving two or more spatially representative data sets with respect to one another are known in the art, and include approaches described in U.S. Pat. No. 5,531,227 (Schneider 1996), U.S. Pat. No. 6,351,573 (Schneider 2002), U.S. Pat. No. 5,891,034 (Bucholz 1999), and U.S. Pat. No. 6,236,875 (Bucholz 2001). The user can use the output of the planning system to predict displacement of the energy field and can select an array position, overall power, and/or relative power levels amongst the coils to ensure stimulation at the desired dose is achieved at the intended target. Alternatively, the planning system might process the data sets to identify the needed stimulation parameters (such as array position, power output, relative power of each coil, pulse frequency and duration) and to control some or all of the stimulating parameters (e.g. by controlling motors associated with a robotic positioning system for the array, and/or by controlling the output parameters of the stimulation pulse). Planning system 600 may be part of the power and control system 6 (FIG. 1A), or it may be a separate system.

In some applications it may be advantageous to move the array during the course of treatment. One example is to re-position the array over the head of the person or animal, including tilting for best access to the target. The pattern of magnetic pulses might be temporarily interrupted for repositioning (as described in the proceeding paragraph) so as to protect areas of the anatomy against unintended simulation. in other example, the array may be moved about the head of the subject during stimulation, either rotating completely around the subject or moving it over a selected 3D region. One reason for moving the array is to cause even more electrical change at the target neural membrane. Another way to accomplish this is to rapidly oscillate the electromagnets back and forth (e.g., a few degrees each way) on the axis that is perpendicular to their radial axes. Another is to alternately displace the site of maximal stimulation, thus in effect having two different pulse rates seen by the tissue, one at the target and the other at various superficial locations.

Figure 7A:
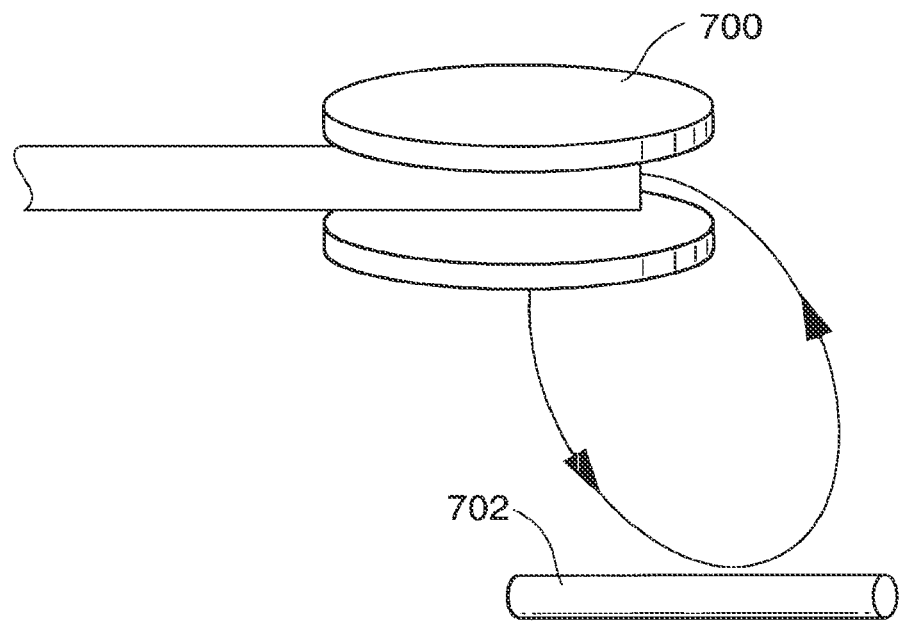
FIGS. 7A and 7B schematically illustrate two examples of movement patterns for moving a coil towards an axon bundle.
Figure 7B:
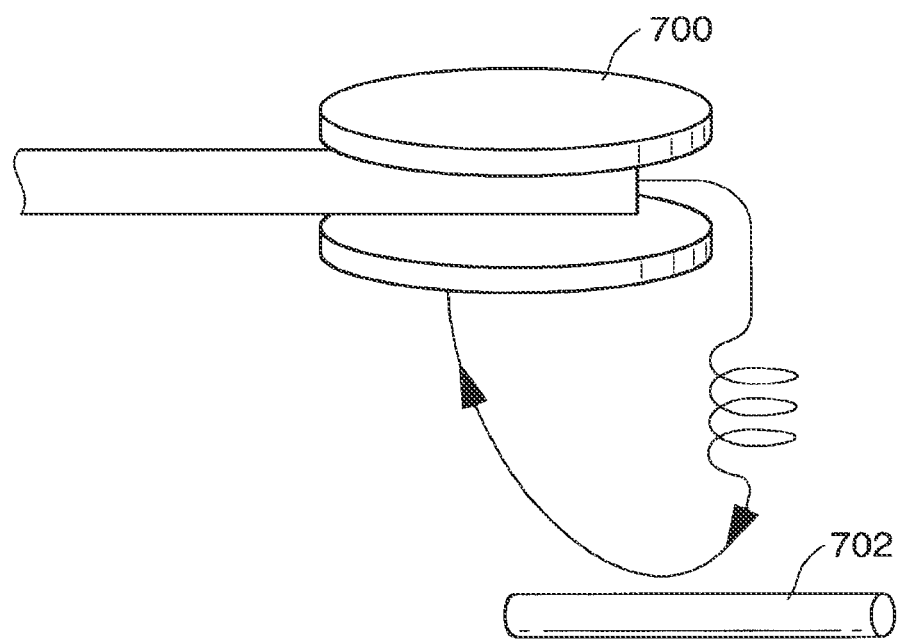

In one embodiment, the path of motion of the coil array related to a target will not be only at an angle relative to an axon bundle, but will preferably be longitudinal as well. This result in an effect akin to "milking" down (or up) the longitudinal axis of that bundle as schematically illustrated in FIG. 7A, in which 700 represents a coil and 702 represents an axon bundle. The axon bundle need not necessarily be straight, but may be curved instead. If curved, the curve may not necessarily reside in a single plane. When using a milking-tipe motion relative to the axon bundle, the motion for the "milking" component of the coil path may consist of a swooping motion that is boring in on the target along a helical path as illustrated in FIG. 7B.

In an alternative embodiment, an array of small electromagnets is used. A higher level of power may be used if the coils are equipped with a cooling mechanism (e.g., liquid nitrogen contained in a reservoir behind the electromagnets). This configuration is more useful in animals that have smaller head sizes because as noted previously, at short distances relative to the size of the electromagnet the magnetic-field profile is determined by the size characteristics or the electromagnet itself. At long relative distances, the magnetic field falls off at a ratio of one over the cube of the distance.

An embodiment that can be used with any number or size of electromagnets is one in which the electromagnets are configured in an appropriately sized helmet having suitable coiling mechanisms for the coils.

While various embodiments of the present invention have been described above, it should be understood that they have been presented by way of example, and not limitation. It will be apparent to persons skilled in the relevant art that various changes in form and detail may be made therein without departing from the spirit and scope of the invention. This is especially true in light of technology and terms within the relevant art(s) that may be later developed. Thus, the present invention should not be limited by any of the above-described exemplary embodiments, but should be defined only in accordance with the following claims and their equivalents.

Any and all patents, patent applications and printed publications referred to above are incorporated by reference.

What is claimed is:

1. A method for applying magnetic field stimulation to a deep brain target, the method comprising the steps of:
   positioning a plurality of bent electromagnetic coils at different locations about a subject's head, each coil comprising a plurality of concentric loops arranged about a normal axis, the concentric loops of each of the electromagnetic coils having a curved shape relative to a plane that is perpendicular to the normal axis such that the plurality of electromagnetic coils conform to the subject's head;
   energizing the electromagnetic coils to produce a plurality of magnetic fields, wherein the coils are positioned such that a normal component of each of the magnetic fields points toward a common convergence point, the common convergence point spaced a distance away from the deep brain target and having a predetermined spatial relationship to the deep brain target; and
   stimulating the deep brain target by summing stimulation from each of the magnetic fields at the deep brain target, wherein the deep brain target is deeper in the brain and further from the electromagnets than more superficial cortical non-target brain regions between the deep brain target and the electromagnetic coils.

2. The method of claim 1, wherein each electromagnetic coil includes at least two loops.

3. The method of claim 1, wherein energizing the electromagnetic coils comprises energizing the electromagnetic coils at different patterns, frequencies, or patterns and frequencies of stimulation.

4. The method of claim 1, wherein positioning comprises placing the subject's head within a frame holding the plurality of electromagnetic coils.

5. The method of claim 1, wherein the plurality of electromagnetic coils are directly adjacent to one another.

6. The method of claim 5, wherein the plurality of electromagnetic coils are not concentric with one another.

7. The method of claim 5, wherein the plurality of electromagnetic coils do not overlap with one another.

8. The method of claim 5, wherein the plurality of electromagnetic coils are attached to one another.

9. The method of claim 5, wherein the plurality of electromagnetic coils are electrically discrete from one another.

* * * * *